United States Patent
O'Driscoll et al.

(10) Patent No.: US 9,244,066 B2
(45) Date of Patent: Jan. 26, 2016

(54) OPTICAL TESTING SYSTEM

(75) Inventors: Stephen O'Driscoll, Dublin (IE); Conor Burke, Laytown (IE); Brian MacCraith, Dublin (IE)

(73) Assignee: DUBLIN CITY UNIVERSITY, Dublin (IE)

( * ) Notice: Subject to any disclaimer, the term of this patent is extended or adjusted under 35 U.S.C. 154(b) by 327 days.

(21) Appl. No.: 14/343,612

(22) PCT Filed: Sep. 9, 2011

(86) PCT No.: PCT/EP2011/065678
§ 371 (c)(1),
(2), (4) Date: Jun. 4, 2014

(87) PCT Pub. No.: WO2012/032171
PCT Pub. Date: Mar. 15, 2012

(65) Prior Publication Data
US 2014/0296112 A1    Oct. 2, 2014

(51) Int. Cl.
*G01N 33/50* (2006.01)
*G01N 21/77* (2006.01)
*G01N 21/64* (2006.01)
(Continued)

(52) U.S. Cl.
CPC .............. *G01N 33/54373* (2013.01); *G01J 1/58* (2013.01); *G01J 3/0202* (2013.01); *G01J 3/0208* (2013.01); *G01J 3/0272* (2013.01); *G01J 3/0291* (2013.01); *G01J 3/28* (2013.01); *G01J 3/4406* (2013.01); *G01J 3/50* (2013.01); *G01N 21/251* (2013.01); *G01N 21/64* (2013.01); *G01N 21/645* (2013.01); *G01N 21/6428* (2013.01); *G01N 21/6486* (2013.01); *G01J 2003/1213* (2013.01); *G01N 21/8483* (2013.01); *G01N 2021/6432* (2013.01); *G01N 2021/7786* (2013.01); *G01N 2201/024* (2013.01); *G01N 2201/0221* (2013.01)

(58) Field of Classification Search
CPC .......... G01J 3/0272; G01N 2021/7756; G01N 2021/0221; G01N 2021/0222; G01N 2021/024
See application file for complete search history.

(56) References Cited

U.S. PATENT DOCUMENTS

| 5,910,421 A * | 6/1999 | Small et al. ................. 435/19 |
| 2006/0222567 A1 | 10/2006 | Kloepfer et al. |
| 2008/0055755 A1 * | 3/2008 | Hillis et al. ................. 359/857 |

FOREIGN PATENT DOCUMENTS

| EP | 2116884 A1 | 11/2009 |
| JP | 2008-286522 A | 11/2008 |

(Continued)

OTHER PUBLICATIONS

International Search Report, mailed Dec. 5, 2011, for PCT/EP/2011/065678, 5 pages.
Written Opinion, mailed Dec. 5, 2011, for PCT/EP/2011/065678, 12 pages.

*Primary Examiner* — Paul Hyun
(74) *Attorney, Agent, or Firm* — Seed IP Law Group PLLC

(57) ABSTRACT

The present application provides a system (1) that comprises a mobile phone (25) to allow testing of samples from a patient at the point of care or environmental/industrial process monitoring tests to be performed in the field. The system (1) may be easily adapted for use with a variety of different mobile phones (25). The mobile phone (25) comprises an integrated camera (15). The system (1) further comprises an optical module (20) for receiving a sample for testing. The mobile phone (25) is configured to extract the intensity and/or color information from the camera (15).

20 Claims, 14 Drawing Sheets

(51) Int. Cl.
*G01J 1/58* (2006.01)
*G01N 33/543* (2006.01)
*G01J 3/02* (2006.01)
*G01J 3/28* (2006.01)
*G01J 3/44* (2006.01)
*G01J 3/50* (2006.01)
*G01N 21/25* (2006.01)
*G01J 3/12* (2006.01)
*G01N 21/84* (2006.01)

(56) References Cited

FOREIGN PATENT DOCUMENTS

| | | |
|---|---|---|
| JP | 2010-190867 A | 9/2010 |
| WO | 2009/060412 A2 | 5/2009 |
| WO | 2009/060412 A3 | 5/2009 |
| WO | 2009/088930 A2 | 7/2009 |
| WO | 2009/088930 A3 | 7/2009 |

* cited by examiner

OPTICAL TESTING SYSTEM

FIELD OF THE APPLICATION

The present application relates to systems having a sensor and in particular to the use of a mobile phone as part of the sensing system.

DESCRIPTION

The sector of point-of-care (POC) diagnostics is experiencing a period of significant growth with increasing efforts in both academic and industrial research environments being expended on the development of low-cost, portable diagnostic devices. These units are intended for deployment in a doctor's clinic or, in some cases, to remote locations, such as patients' homes. The development of these devices is desirable in improving the quality of life for individuals suffering from chronic illness by minimising the intrusiveness of management and monitoring of their condition, including reducing the frequency of hospital visits.

Current devices are designed for specific uses and are relatively expensive. The present application seeks to provide an alternative lower cost system.

One low cost approach which has been suggested is to employ a camera phone as part of a visual test, for example the camera of the phone may be employed to capture an image of a colour based sensor such as, for example, litmus paper. The image of the litmus paper may then be analysed to determine the colour of the litmus paper thus replacing the conventional approach of a user performing a visual comparison with a reference chart. In contrast to the custom designs employed in point of care diagnostics described above, this approach is relatively inexpensive as it simply employs the camera of a phone to capture an image of the test result. This approach may be used with most applications where a test is performed visually by a user and allows for an inexperienced user to perform a visual test.

SUMMARY

The present application is directed to a novel testing system employing a personal communications device with an image sensor, i.e. a camera. The camera is employed as an intensity/colour sensor and the personal communications device analyses the intensity/colour to provide a measurement to a user. The testing system may be employed in chemical and biological sensing applications, including fluorescence-based techniques.

In contrast to prior art approaches where the camera of a mobile device was used to provide an image of a test, the present application employs a non-imaging approach in which the camera of the mobile device is used as a photodetector rather than its conventional use as an imaging device.

Accordingly, the present application provides a system in accordance with the claims which follow.

In another embodiment, an optical testing system is provided comprising: a personal communications device having an integrated camera; a docking cradle being shaped to receive the personal communications device, the docking cradle being further configured for connection with an optical module; an optical module being configured to receive a sample for testing and being further configured to collect and direct light from the sample to the camera, wherein the personal communications device is configured to extract the intensity and/or colour information from at least one pixel on the camera and to provide a measurement to a user from said at least one intensity and/or colour measurement. The system may further comprise means for illuminating the sample within the testing system, optionally the means for illumination comprises an integrated light source within the personal communications device. In turn, the integrated light source may be one of:
a) a light, b) a flash, and c) a display screen.

The system may be configured to set the colour or intensity of the integrated light source to a predetermined value when performing a measurement.

The system may be configured to measure a plurality of samples and in this case, the optical element suitably comprises a plurality of outcouplers, each outcoupler extracting light from an individual sample/sample area and facilitating its direction onto a unique area of the camera.

The system may further comprise an optical sensor chip, wherein the optical sensor chip is configured to provide luminescence in response to the presence of a chemical or biological substance in a sample provided to the optical sensor chip. The optical sensor chip may be configured to provide an intensity and/or colour change in response to the presence of a chemical or biological substance in a sample provided to the optical sensor chip. In one arrangement, a plurality of wells/spots are provided on the optical sensor chip, each well/spot being configured to provide luminescence in response to the presence of a chemical or biological substance in a sample provided to the well. In a further arrangement, a plurality of wells/spots are provided on the optical sensor chip, each well/spot being configured to provide an intensity and/or colour change in response to the presence of a chemical or biological substance in a sample provided to the well.

The system may be suitably configured to measure one or more of: oxygen, carbon dioxide, ammonia, carbon monoxide, nitrogen dioxide, lead, ozone, sulphur dioxide, dissolved oxygen, dissolved carbon dioxide, dissolved ammonia, pH, cadmium, mercury, chromium, nitrate, nitrite, metal ions, cations, nitric oxide and Volatile Organic Compounds (VOCs). Equally, the system may be configured to detect one or more of antibodies, antigens, proteins, DNA, RNA, mRNA, siRNA, miRNA, aptamers, pathogens and cells.

The software on the personal communications device may be configured to correct the pixel intensity and/or colour information using calibration information stored locally in a calibration file. Where this is the case, the calibration information may be obtained during a calibration procedure performed locally on the testing system. Similarly, the calibration file may at least be partially downloaded from a remote location.

The docking cradle may comprise a phone mating section being shaped to receive the body of personal communications device in a first direction and a docking section mountable on said phone mating section in a second direction transverse to the first direction. In which case, each of the phone mating section and the docking section may have openings defined therein to allow light from the optical module to pass there through to the camera of the communications device.

The optical module may further comprise a cover having a plurality of inlet and outlet ports that facilitate the delivery of liquid samples to the optical sensor chip.

These and other embodiments, features and advantages will be further understood and appreciated from the drawings which follow.

DETAILED DESCRIPTION

The present application provides for quantitative optical sensing using a personal communications device, such as for example a mobile phone. A general requirement for the present application is that the personal communications device possesses an in-built image sensor, i.e. a camera. Whilst the application is not limited to a phone per se and may, for example be an equivalent device without the phone functionality but having another mode of communication, e.g. Wi-Fi. Furthermore, the device must possess sufficient data processing capability and have a means of being programmed to analyse data from the camera. In summary, the personal communications device should have a camera, means for being programmed to analyse data acquired from the camera and then means for communicating the results of this analysis.

Figure 1:
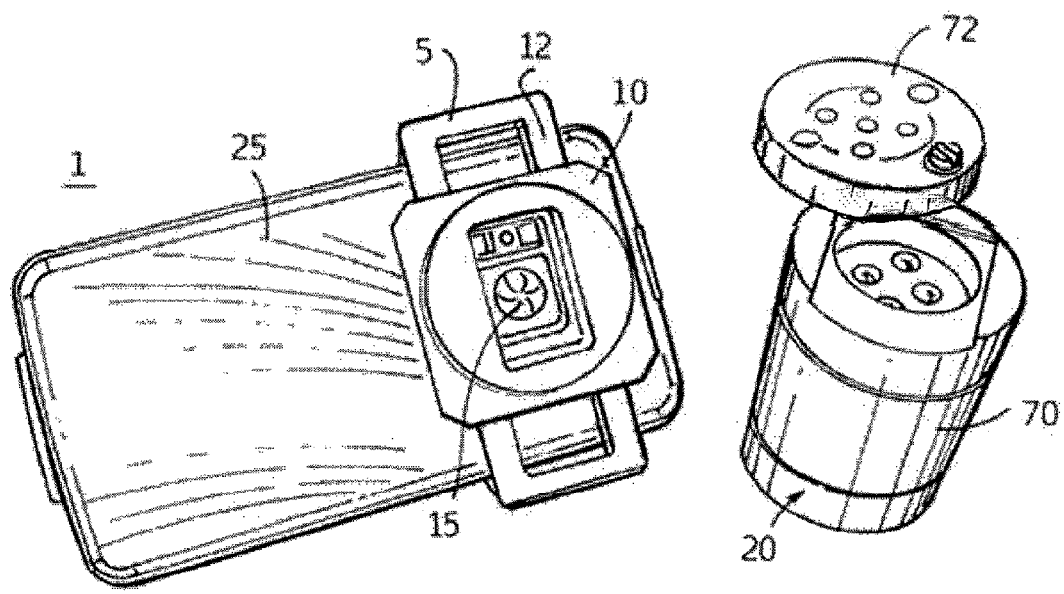
FIG. 1 is an exemplary arrangement of a sensor system shown partially assembled including a mobile phone according to a first embodiment.
Figure 2:
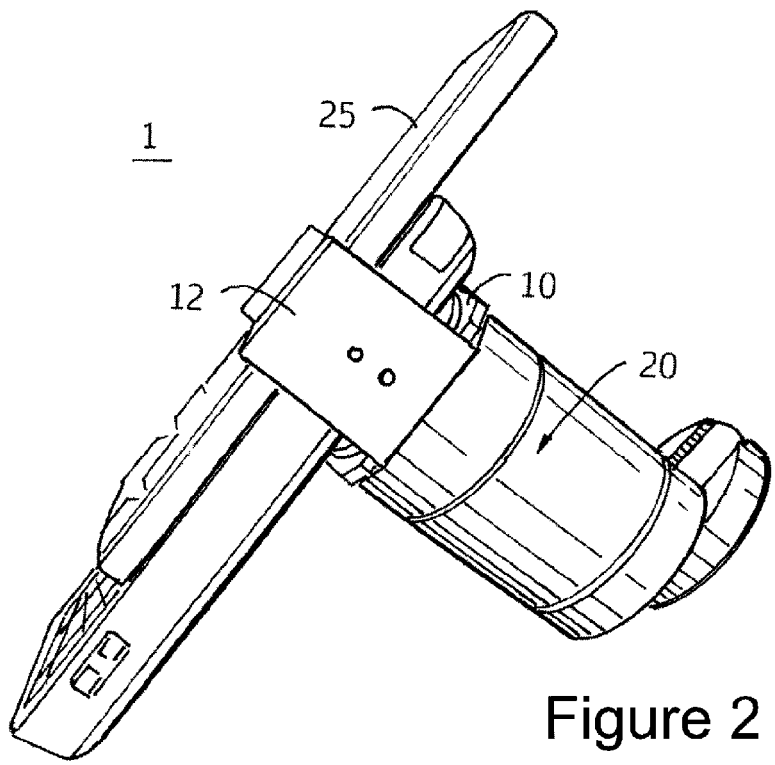
FIG. 2 is view of the system of FIG. 1 in an assembled state.

However, for the purposes of explanation, the description will now proceed by referring to a personal communications device as a camera phone, which is the preferred implementation. The system comprises a docking cradle arrangement 5, as shown in FIGS. 1 and 2, which is suitably shaped to receive and retain at least the portion of the camera phone 25 body housing the phone's camera 15. The docking cradle in turn may be detachably connected or integrally formed with an optical module 20. The optical module may contain an integrated sample holder or is dimensioned to receive a sample holder, which houses an optical sensor chip. The sample holder may have an opening through which the optical sensor chip may be inserted. Other configurations may also be used. For example, the optical module or the docking cradle may have a recess on one of their surfaces for receiving the sensor chip. Once inserted in such a recess, the optical module and docking cradle may be connected together. In any event, it will be appreciated that a purpose of the docking cradle—optical module arrangement is such that the optical sensor chip is positioned such that light originating from the chip (e.g., fluorescence) and collected by the optical sensor module is directed onto the camera. It will be appreciated by those skilled in the art that the sensor chip may be aligned with (i.e., centred on) the optical axis of the camera or that it may be located off-axis and the emitted light signal delivered to the camera either directly through one or more lenses and/or indirectly by means of optical fibres or reflectors such as a mirror.

Figure 3:
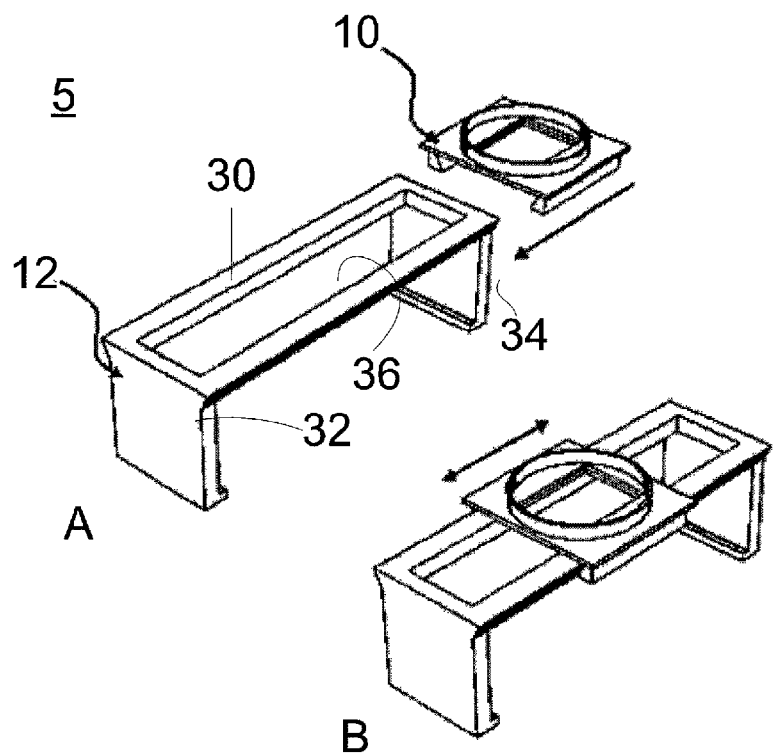
FIG. 3A and FIG. 3B illustrate the mode of assembly and operation of an exemplary docking cradle for use in the system of FIG. 1.
Figure 4:
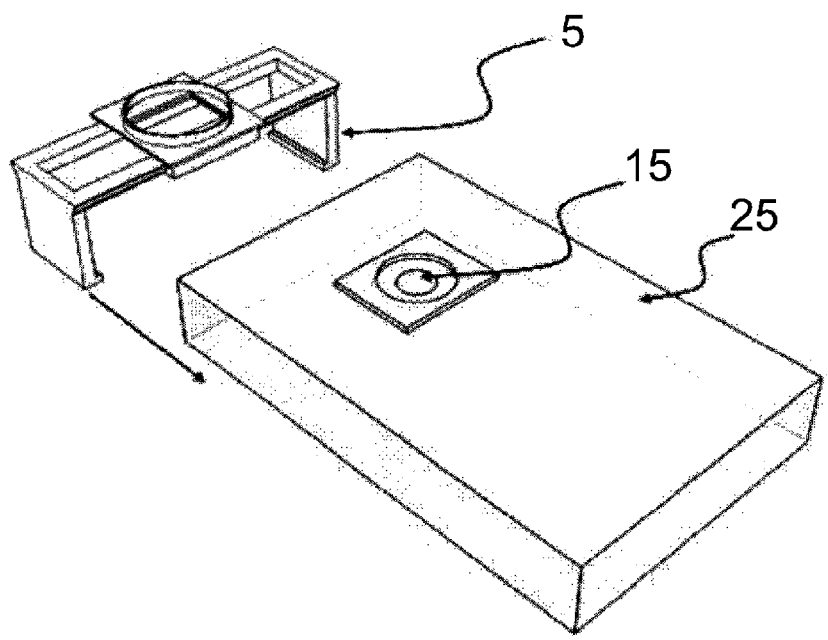
FIG. 4 illustrates the manner of attaching the exemplary docking cradle to a mobile phone.
Figure 5:
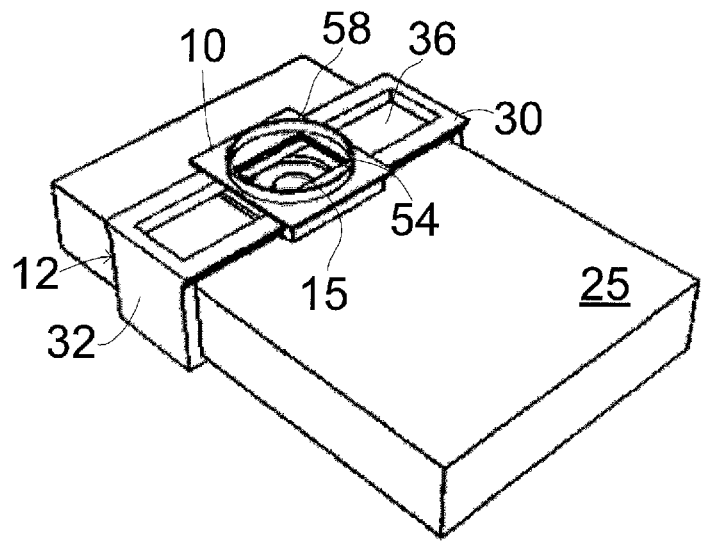
FIG. 5 illustrates the exemplary docking cradle attached to a mobile phone.
Figure 6:
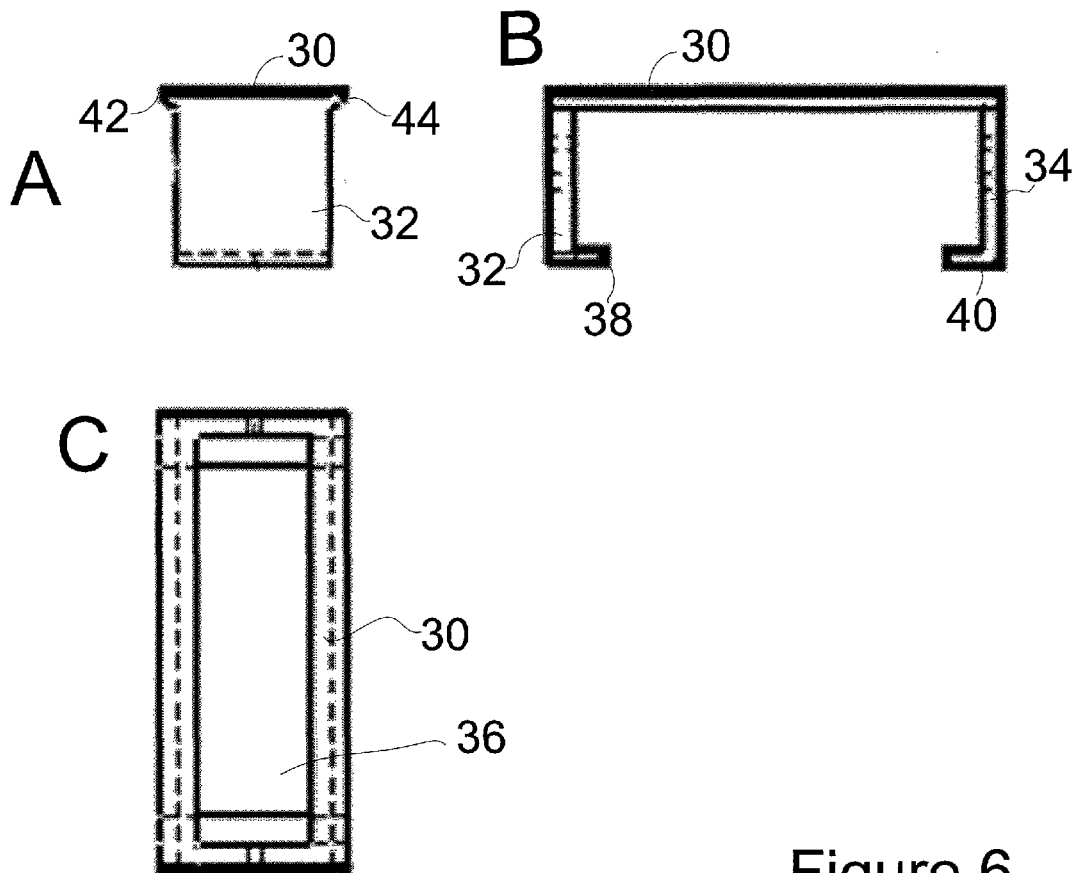
FIGS. 6A, B and C illustrates side, front and top views respectively of a rail section of the exemplary docking cradle of FIGS. 3A and 3B.
Figure 7:
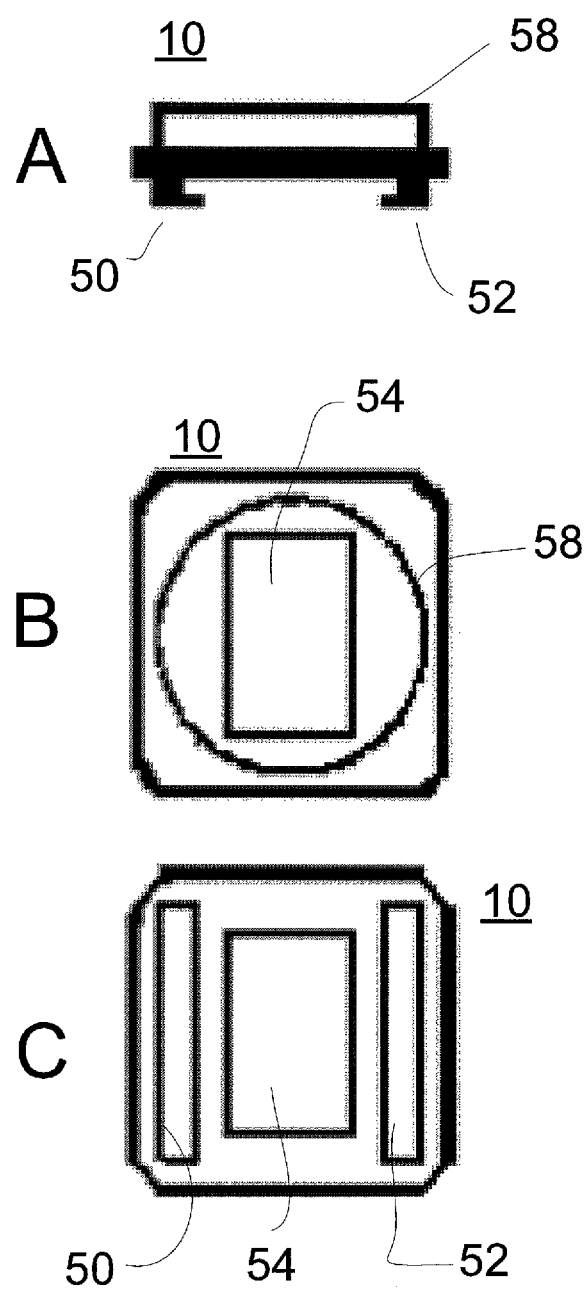
FIGS. 7A, B and C illustrates side, top and bottom views respectively of a docking section of the exemplary docking cradle of FIGS. 3A and 3B.

In the exemplary docking cradle arrangement 5, shown in FIG. 3(A-B), the docking cradle comprises a phone mating or rail portion 12 and a docking section 10. The phone mating portion is configured to engage with the sides of the phone as shown in FIG. 4 and the assembled state is shown in FIG. 5. The phone mating portion is substantially C-shaped with a planar body 30 and two arms 32, 34. The planar body is slightly longer than the width of the mobile phone with which it is intended to mate and similarly the arms are slightly larger than the thickness of the phone. This configuration allows for the phone mating portion to be slid onto and along the communications device. Once suitably positioned, the rail mating portion may be held in place by a retaining feature, for example a resilient feature such as a spring or grub screws or the like which may be provided on the body of the rail mating portion. In use, the phone mating portion is slid onto and along the phone to the location of the camera lens on the phone body. Small retaining portions, i.e. flanges 38, 40 shown in FIG. 6 may be provided at the end of each arm 32, 34 to ensure the phone mating portion is retained on the phone. An aperture 36 is defined in the planar body. This aperture provides an opening through the planar body to the camera lens of the phone. The aperture 36 suitably extends from one arm to the other so that an opening may be provided to the lens irrespective of where the lens is positioned on the face of the phone.

The edges 42, 44 of the planar section define rails with which corresponding rail retaining features 50, 52 of the docking section may engage. The edges may be chamfered. In use, the docking section may be slid on to the planar section at the side and then along the phone mating portion. The docking section may be held in place using grub screws or other retaining features provided on this section. The docking section 10 also has an opening 54 defined in it. When positioned correctly on the phone mating portion on the phone, this opening is aligned with aperture 36 in the phone mating portion and in turn provides the camera with an unobstructed field of view. The docking section has a docking feature 58 allowing the docking cradle to engage with a corresponding docking feature on the optical assembly. The engagement between the docking features may be a friction fit, a threaded connection or other suitable arrangement. It will be appreciated that the above described docking arrangement provides an easy and reliable method of aligning the optical module with the camera lens. In particular, it will be appreciated that the docking cradle may be placed on the phone and then positioned to ensure that the camera lens is visible through the aperture of the planar section of the phone mating portion and the docking section. Once positioned correctly, the optical module may be connected to the docking portion. The flexibility offered by this approach means an individual docking cradle may be used on similar sized phones on which the camera locations vary. Moreover, it will be appreciated that different phone mating sections may be provided for different widths\thicknesses of phone with the same docking section. In each case, the dock and phone mating portion may be positioned correctly on the phone body so that the camera lens is visible through the aperture(s) of the docking cradle. The optical assembly, which is described in greater detail below, may then be mounted on the docking cradle so that an analysis may be performed.

Whilst separate phone mating sections may be provided in order to accommodate different phone models, in an alternative arrangement (not shown), an adjustable gripping mechanism may be employed that accommodates a range of phone widths and thicknesses. An important feature of the present system is that the analysis performed by the camera phone of an inserted sample is not concerned with the shape or similar characteristics of the sensor chip within an image. Instead, the camera is simply being used as a photodetector for measuring the intensity and/or colour of an optical signal emitted from a particular point/location (or points where several samples are provided on one sensor chip) from the sensor chip. It will be appreciated that depending on the detector technology employed in the phone, the camera may use a CCD or CMOS image sensor comprising a plurality of individual light-sensitive pixels. For the purposes of the present application, the nature of the sensor is relatively unimportant. It is sufficient that pixel data is accessible and may be related to light intensity and/or colour.

The present application employs the camera simply as a collection of individual photosensitive elements. Each of these elements is capable of producing an electronic signal that may be related to the number of photons incident upon it. As such, the camera is viewed as an arrangement of individual photodetectors. This allows the use of the phone's camera for quantitative optical sensing applications that employ non-imaging optical configurations, in contrast to prior art where the camera is viewed merely as a photographic device. Thus, for example, the present application is suited to the measurement of florescence from a test sample.

In this context, light intensity may include that of one colour or of multiple colours. Other information, i.e. intensity information for non-measurement locations is discarded. Thus it is a considerable advantage, although not an essential requirement, that the data from the camera be available to applications in an unprocessed (raw) format, as otherwise the accuracy of the measurement might be impaired by subsequent processing. For example, the application of compression algorithms, such as JPEG, which reduce the information content in the image, for efficient storage and transfer or automatic brightness and contrast functions. Once an intensity and/or colour measurement has been obtained it may be analysed for meaning and a result provided on the screen of the device to the user and/or the result transmitted to another location for review (e.g. a doctors' surgery). Where access to individual pixels of the camera is available, traditional approaches involving the capture of an entire image are not necessary and the software may simply access an individual pixel intensity and/or colour measurement directly from the area of interest of the camera.

The individual components of the optical module and its use will now be described in greater detail. The optical module is suitably configured to receive an optical sensor chip. Suitably, the optical sensor chip may be or resemble a glass microscope slide 81 with one or more wells/spots formed thereon from where measurements may be taken. In use, the camera 83 of the phone is used to detect the optical signal from the sensor chip and more specifically the wells/spots. The sensor wells/spots are suitably configured to undergo a change in their optical properties, e.g. luminescence, in response to the presence of a chemical or biological substance in the measurement environment, e.g., air, water or blood. It will be appreciated that a variety of materials are known for this purpose. For example, preliminary experiments carried out by the present inventors implemented a fluorescence-based oxygen sensor in which the spots comprised a sol-gel thin film doped with ruthenium tris(diphenylphenanthroline) which is a well-known, oxygen-sensitive fluorescent complex. The use of such a sensor is based on the principle of fluorescence quenching, which means that increases in oxygen concentration reduce the fluorescence 87 intensity emitted by the sensor. In the experiment, this change was readily determined by the camera.

It will be appreciated by those skilled in the art that a variety of different luminescence sensors and applications thereof are applicable to the present system, for example the presence/absence of luminescence may be indicative of the presence/concentration of a target analyte/molecule at an individual sensor. This analyte may be a chemical or biological species of interest, e.g., antibody, antigen, DNA, gas molecule, enzyme, cell, hormone etc.

More specifically, the present system may be employed in a number of different applications, for example it may be used in environmental monitoring to detect oxygen, carbon dioxide, ammonia, carbon monoxide, nitrogen dioxide, lead, ozone, sulphur dioxide, dissolved oxygen, dissolved carbon dioxide, dissolved ammonia, pH, cadmium, mercury, chromium, nitrate, nitrite, metal ions & cations.

It may also be used in biomedical applications, for example, analysis of a fluid sample from a person, including, for example, their breath condensate, blood, saliva, urine or sweat. The fluid sample may be analysed for the presence of particular molecules including, for example, oxygen, carbon dioxide, ammonia, nitric oxide, Volatile Organic Compounds (VOCs). In such scenarios, the person being tested would blow either directly or indirectly upon the sensor chip, which thereafter would be tested using the present luminescence system.

Figure 8:
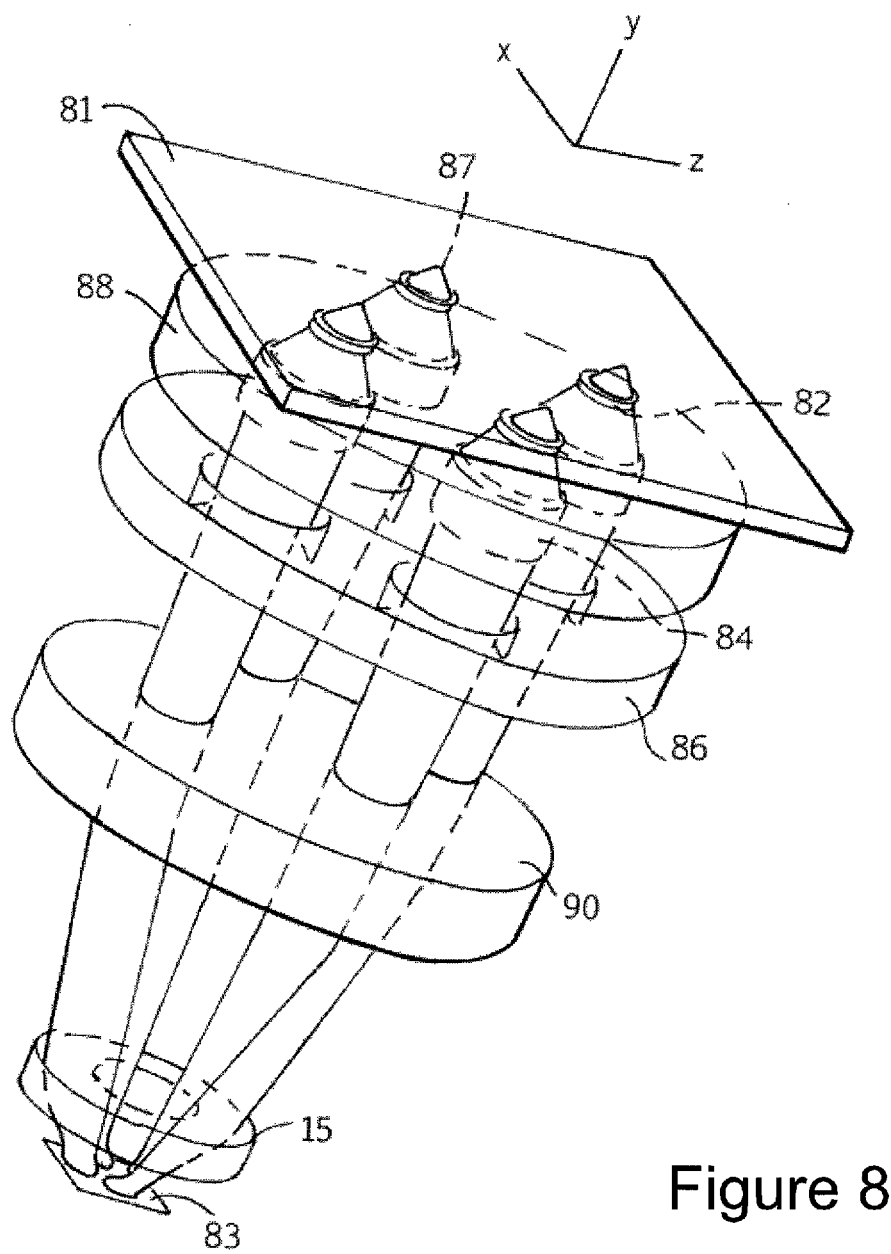
FIG. 8 is an illustrative representation of the optical arrangement of an optical module for use in the system of FIG. 1.
Figure 9:
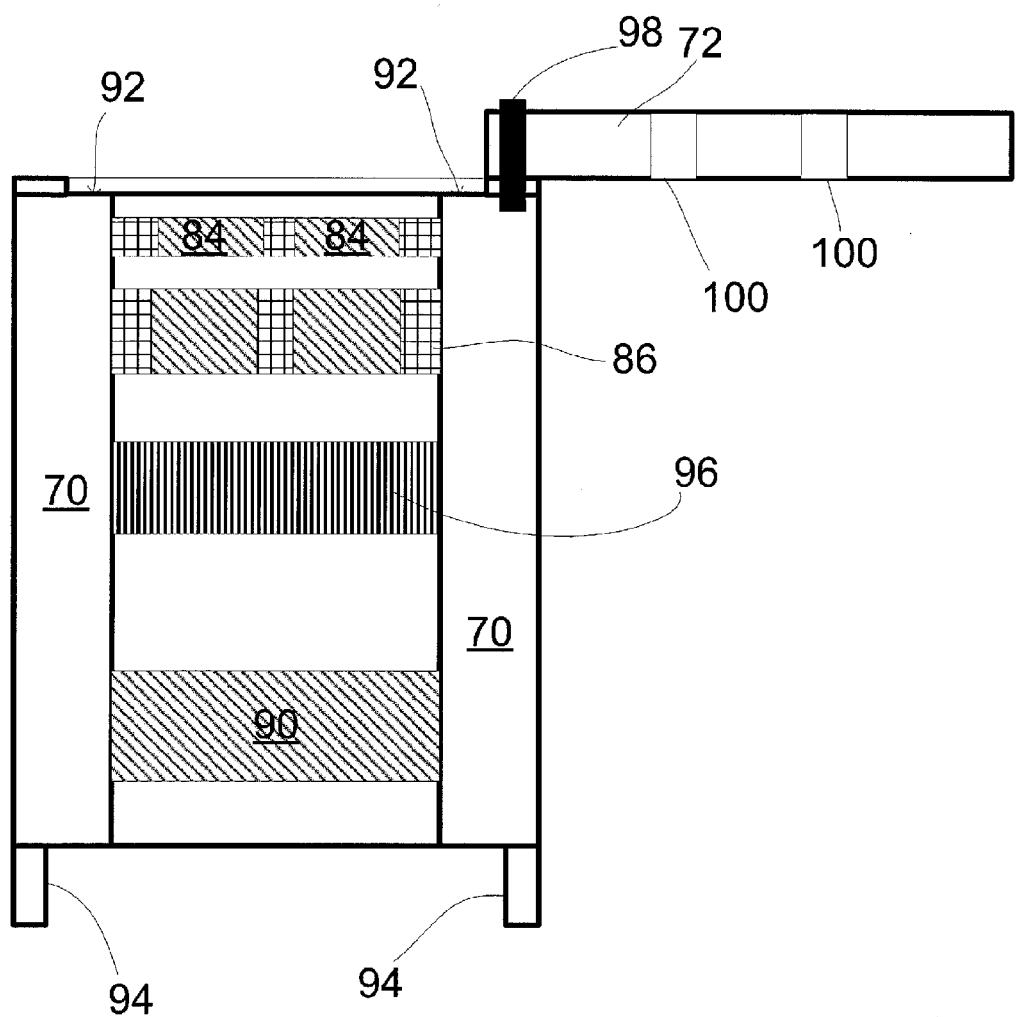
FIG. 9 is a cross sectional view of an exemplary optical module for use in the system of FIG. 1.

Similarly, the sensor chip may be selected to allow for the detection of Antibodies, antigens, proteins, DNA, RNA, mRNA, siRNA, miRNA, aptamers, pathogens (e.g., bacteria, viruses, protozoa), cells (e.g., platelets, monocytes) by means of luminescence as would be familiar to those skilled in the art. The optical assembly, which is configured to receive the sensor chip, is in turn suitably attached to the camera phone by an alignment means, such as the docking cradle as previously described. The primary purpose of the docking cradle is to ensure the camera is optically aligned with the optical sensor chip to allow delivery of light from the sensor to the camera. It will be appreciated that other methods may be provided which include an alignment feature that allows the camera of the phone to be aligned with the non-imaging optics. Similarly, the alignment means may include features which restrain the camera from moving relative to the non-imaging optics such as provided for in the previously described docking cradle. The optical module is designed to collect the optical signal from one or more locations on the optical sensor chip and direct this signal onto the camera. The purpose of the optical module is not to construct an exact image of the optical sensor chip but simply to ensure the effective transmission of the optical signal from one or more discrete areas on the sensor chip onto one or more discrete areas of the camera without permitting any mixing or overlap of the signal from individual well/spot locations during transmission from the sample to the camera. Suitably, the optical module comprises a lens arrangement for directing the optical signal from the wells/spots onto the camera, which conventionally comprises at least one lens and an image sensor. In respect of the lens arrangement, a separate lens may be employed for each spot, e.g. using a lens array. The optical module may also include one or more filters to eliminate unwanted wavelengths of light. Thus, in the exemplary arrangements of FIGS. 8 and 9, the optical module comprises a main body 70 and a cover 72. The base of the main body has mating features 94 which are configured to co-operate with and mate to corresponding features 58 on the docking cradle. The top of the main section is provided with receiving features 92 defining a space for receiving the optical sensor chip (slide) and which in turn aligns the wells or spots of the sensor chip with corresponding optical components in the optical assembly. The cover 72 may be rotatably fixed by means of a suitable hinge 98 to the top of the main body allowing the cover to be swung into place above an optical sensor chip that has been received in the top part of the main body. The main body of the optical module houses one or more lenses and filters. In the exemplary arrangement shown, there are a plurality of wells/spots on the sensor chip and the optical module provides an optical train of lenses and filters for each well\spot providing a separate optical path for each well\spot. More specifically a first set of individual lenses 82 are provided as the entry point into each train. These lenses may be provided as part of the optical sensor chip 87 or in a suitable mount. The lenses are selected to act as outcouplers, with the goal of extracting as much light as practicable being emitted from the individual wells/spots. It will be appreciated that these lenses 82 act to enhance the amount of light transmitted though the optical sensor chip from the wells/spots. An example of a suitable outcoupling lens is the NT43-398 PCX lens available from Edmund Optics. It will be appreciated that the outcoupler may be located on the lower surface of the optical sensor chip and directs light into the optical assembly. The outcouplers enhance the amount of light (e.g., fluorescence) that is transmitted through the optical assembly. To operate in this way, the lens is suitably positioned so that the sample lies between the focus of the lens and the lens. It will be appreciated that this results in a non-imaging operation of the lens, since the spot is at a distance from the lens that is less than the focal length of the lens. This ultimately prevents an image being formed at the camera, but allows the amount of light that can be collected to be enhanced. The outcoupler lenses may be formed as part of the optical sensor chip or mounted thereto or in contact therewith suitably for example using an index matching fluid. A second set of lenses 84 is provided and suitably mounted below the first set. The second set of lenses collects the light transmitted through the outcoupler lenses and produces near-collimated beams for each of the wells/spots, thereby acting as pickup lenses or a light collection optic. The collimated beams of light are directed through a beam spatial filter 86, which is suitably a layer of substantially opaque material with an aperture defined for receiving each collimated beam. The beam spatial filter reduces interference\mixing of light beams coming from adjacent wells/spots. A final lens or group of lenses 90 focuses the light from each of the wells onto the camera lens 15, which in turn focuses the light beams on to the camera of the mobile device. The final lens 90 may be any focussing lens, for example a double convex (DCX) or plano convex lens. An emission filter 96 (shown in FIG. 9) may be provided between the second set of lenses and the final lens 90 in order to provide spectral discrimination of the fluorescence emission and excitation signals. The use of the second set of lenses producing a collimated beam facilitates efficient filter performance due to the dependence of many filter types (e.g., interference filters) on the incident angle of the light that is transmitted through the filter. During typical operation, the sample (e.g., blood or saliva) to be tested may be placed on an optical sensor chip (which may comprised simply of a glass/polymer slide) on which a number of sensing locations have been patterned (e.g., sol-gel sensor spots, immobilised biomolecules etc.). After application of the sample to the optical sensor chip, the optical sensor chip may be inserted into the module for analysis. Alternatively, the sample may be delivered to the optical sensor chip while it is housed in the module using a fluidic delivery arrangement with an appropriate fluidic manifold 100 containing inlet and outlet ports for the sample. It will be appreciated that whilst lens 90 has been described as the final lens that this is only by way of example and that further lenses or optical features may be provided. For example, further lenses may be employed to reduce the diameter of the one or more beams and for assisting in the focussing of the light onto the sensor of the camera.

Figure 14:
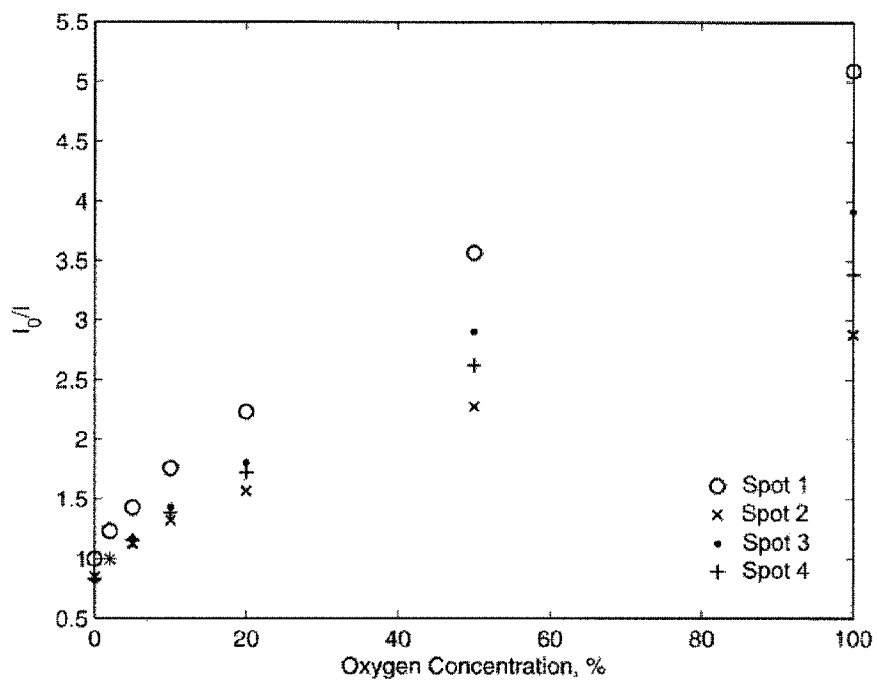
FIG. 14 is the measured response of 4 oxygen-sensitive sensor spots as recorded by the system of FIG. 1.

Following acquisition by the camera, the digitised optical signal may be analysed to identify the features corresponding to the optical signal (e.g. fluorescence) detected from each of the wells/spots on the optical sensor chip. Techniques for performing such an analysis would be familiar to those skilled in the art of signal processing. Thus for example, a signal may be examined for values exceeding a minimum signal threshold value that has been determined to correspond to an optical intensity of interest. Once signal components of interest have been identified, individual signal values corresponding to wells/spots may be identified by a mask and measurements corresponding to wells/spots obtained. Thus for the exemplary signal acquired from the wells/spots of an optical sensor chip that might be acquired by the camera, a corresponding mask developed by using a threshold value is shown in FIG. 14. This mask may be used to perform a measurement at a particular well/spot by excluding pixel values from the measurement not defined by the mask. For some sensing techniques, excitation of the sample may be required (e.g. fluorescence applications). This requires that the sample be excited by a suitable light source (e.g. LED). For example, in some fluorescence applications, the use of a light source such as a LED may be desirable. In one embodiment, it is envisaged that for such applications, the sensor module may contain a light source along with any required optics (e.g. filter) and a power supply.

In an alternative arrangement (not shown), the LED/flash or the electro-luminescent display screen of the phone itself may be used as the light source for excitation. This approach is attractive, because it provides an excitation source that is both controllable (by the software application) in terms of spatial location, colour and excitation duration but also utilises the power supply of the phone. In this arrangement, the docking cradle or a separate attachment may include optics for directing light from the LED/Flash or the display to the sample, e.g. using one or more fibre optics. It will be appreciated that such optics may be employed to ensure that light is directed at the samples from an optimum angle.

Arrangements may be put in place to ensure stray light from the LED/flash or the display does not fall upon the camera. Where the LED/flash/display is employed, a calibration routine may be employed to calibrate the camera phone. For example, a calibration optical sensor chip having specific features defined thereon may be presented. As the features of the calibration optical sensor chip would be predefined and known, calibration data may be calculated from the measurements. A particular advantage of using the display of the phone as an excitation source is that different wavelengths (colours) of light may be selected programmatically using software. The ability of such a display to produce multiple excitation wavelengths has been demonstrated and an example is illustrated in FIG. 10, which shows the typical spectral output characteristics of an iPhone 3G display.

Figure 10:
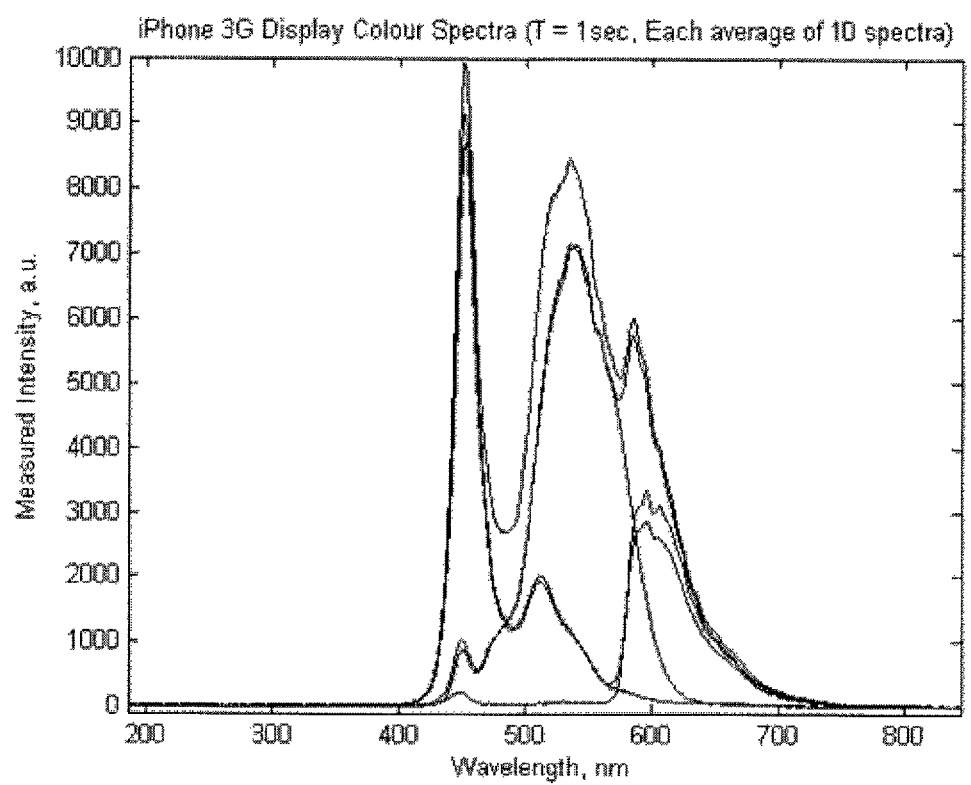
FIG. 10 illustrates the measured spectra from a mobile phone display with the display set to output different colours.

To obtain the emission spectra shown in FIG. 10, one end of an optical fiber was coupled to the screen of an iPhone 3G. The other end of the fiber was then connected to the input of a spectrometer (StellarNet) thereby allowing light emitted by the screen to be spectrally resolved. An iPhone software application (or App) was used to change the colour of the screen. For each selected colour, the spectrometer acquired ten spectra which were then averaged to reduce noise effects. Each spectrum was then displayed on the same axes for comparison. It will be appreciated that this is not unique to the iPhone™ and may be replicated for other phones. Thus for example, the optical sensor chips may be configured for excitation by a first colour (wavelength) which the display may be selected to emit, e.g. by selectively only activating pixels of a particular colour (e.g. red, green or blue) and then taking measurements of light coming from the optical sensor chip using a sensor responsive to a different colour (wavelength) of light. One or more optical filters may be provided to filter the light from the flash and/or display before being directed to the sample. In this respect, it will be appreciated that light may be directed to the sample by introducing it through a side wall of the optical sensor chip in situations where the optical sensor chip comprises a glass slide or similar. An alternative approach is also provided which is set forth in greater detail below.

One of the key features of modern mobile phones that makes the present application possible is that they are programmable. This allows software applications that integrate phone functionality and analysis algorithms to be developed for execution on the phone. In this invention, the data recorded by the phone's camera is accessed through a set of software functions made available by the handset's manufacturer (e.g., Nokia). These functions can be incorporated into custom-written software applications that are coded in a high-level programming language such as C/C++ or Java ME™. Once written, this code is then deployed to the phone where it is available for on-board execution. This functionality may then be combined with other algorithms to form more complex analysis applications. Whilst this is possible using a low-end handset, it will be appreciated that greater processing capability and functionality is available on smart phones (e.g., phones running the Symbian™ OS) enabling the development of high-end software applications. This makes it possible to access, with greater flexibility, the data recorded by the camera and perform advanced analysis on these data using programs, written in languages such as C/C++, that run on the phone. For this reason, such smart phones are particularly suitable for the present application.

Detector Correction

In order to obtain an accurate measure of the number of photons that arrive at a single pixel or group of pixels, it is beneficial, although not essential, to perform a number of corrections to the data produced by the photodetector. One such correction may be referred to as background correction. Typically, when a pixel is not exposed to light an electronic signal will manifest in the pixel. This signal may be due to an offset voltage applied to the pixel or it may be due to thermal noise. When the pixel is exposed to light, the signal produced in the pixel is a combination of the signal due to incident photons and the background signal. Consequently, any measurement of the optical signal made using the pixel values will over-estimate the optical signal due to incident photons if correction is not carried out. Furthermore, this background value may not be constant across the camera and may include random variations between pixels. To correct for this background signal, the background signal must first be estimated. Typically, this process involves the use of pixels in the vicinity of those upon which the optical signal is incident but not directly exposed to the optical signal. The values in these pixels may be processed to reduce the statistical uncertainty (e.g., averaged) before the background level can be estimated. This estimate may then be used to determine the total background contribution in the pixels of interest and then subtracted to give a more accurate measurement of the optical signal.

Other artefacts associated with variations in pixel sensitivity or due to effects associated with the optical path travelled by light to the camera (e.g., uneven excitation source illumination or optical vignetting) can also affect measurement quality. A standard technique called "flat-fielding" may be used to correct for such artefacts in such a camera. Using this approach, the photodetector is exposed to a uniform "test" scene and the illumination variation measured. Typically, a number of images of this test scene are acquired and each image is normalised by the average pixel value. These images are then combined to reduce statistical variation and may also be filtered to remove other noise features. This image is often referred to as a "flat". To remove the aforementioned artefacts before a measurement is performed, the camera pixel values are divided by the corresponding pixel values in the flat.

Employing such techniques, the data value p in a pixel indexed j generated by incident photons can be given by:

$$p_j = \frac{S_j - B_j}{F_j}$$

where $S_j$ is the measured data value of the pixel, $F_j$ is the flat-field correction for the pixel and $B_j$ is the background value. From this definition, the measure of the total optical signal P in an arbitrary arrangement of N pixels is given by:

$$P = \sum_{j=1}^{N} w_k \cdot p_j$$

where $w_j$ is a weighting factor assigned to each pixel that estimates that pixel's contribution to the total signal, P. Here, the weighting factor corrects for pixel sampling effects. This analysis can also be performed on phone.

System Calibration

In addition to performing such corrections to the pixel values, it is also necessary to determine the response of the pixels to a range of known optical intensity/colour values in order to infer unknown values of a sample at a later stage. For this reason, it will be appreciated that a calibration procedure may be provided in the application for use with a corresponding calibration sensor chip, which provides a known measurement or set of measurements. Measurements made using such a sensor chip may be employed to characterise the response of the optical sensor system. It will be appreciated that cameras may vary both from phone model to phone model and indeed from individual phone to individual phone. The use of detector correction and calibration procedures is important in standardising the performance of an in individual system. The use of one of more calibration sensor chip allows for correction data—including correction for background, uneven excitation and linearization of acquired data—to be obtained for and stored on a phone. They also allow for calibration of sample illumination where this illumination is provided by the camera. It will be appreciated that other features may be included for such reference purposes including the use of a test site on the sensor chip where light from the excitation source is directed at the sensor for use in determining a reference level from which individual values may be referenced.

Calibration Procedure

Figure 11:
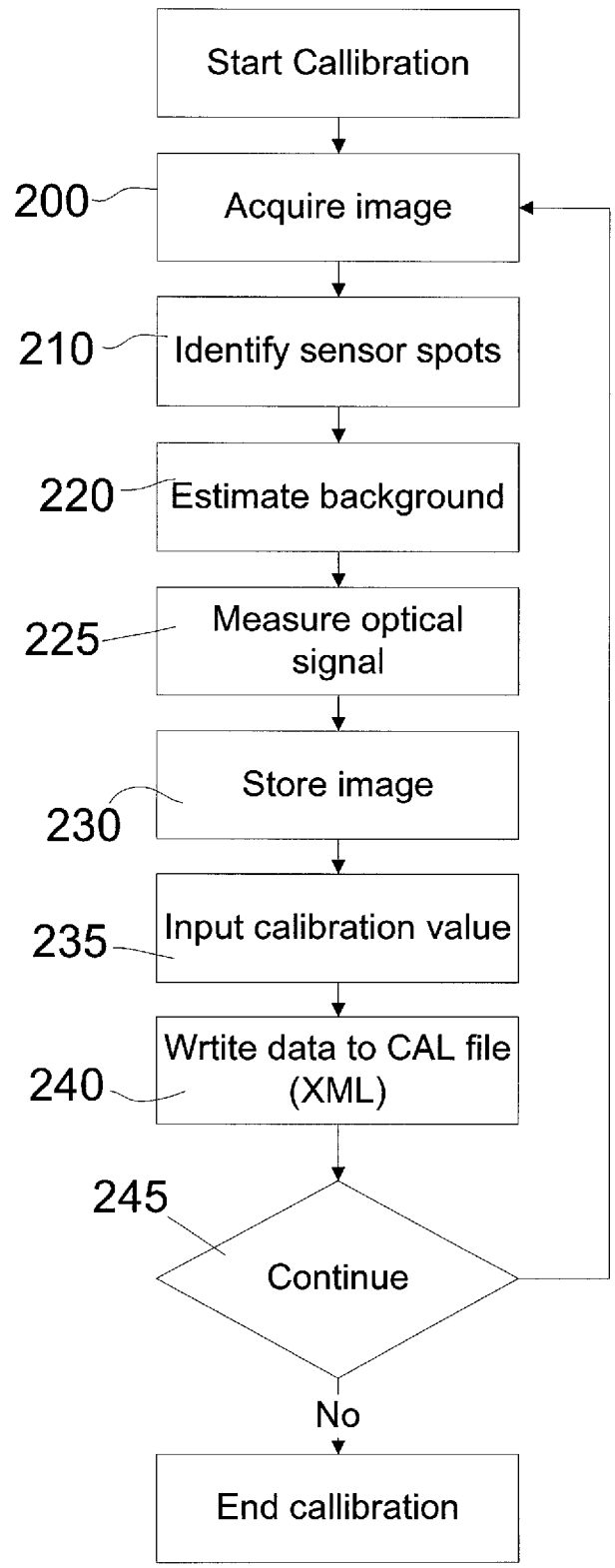
FIG. 11 is a flowchart of an exemplary calibration method for use in the system of FIG. 1.
Figure 12:
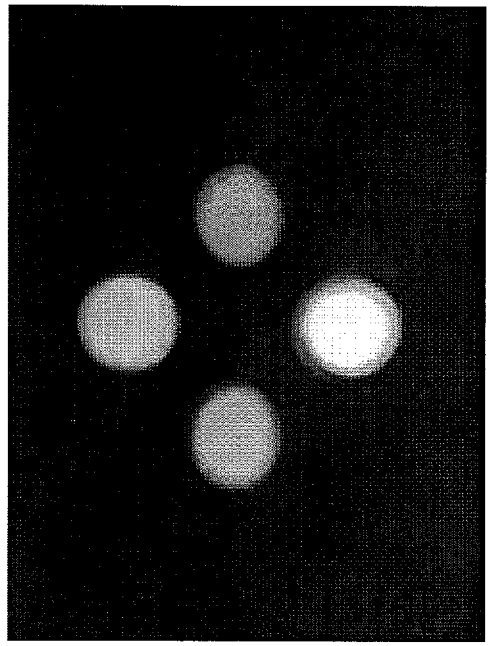
FIG. 12 illustrates a signal acquired using the system of FIG. 1.
Figure 13:
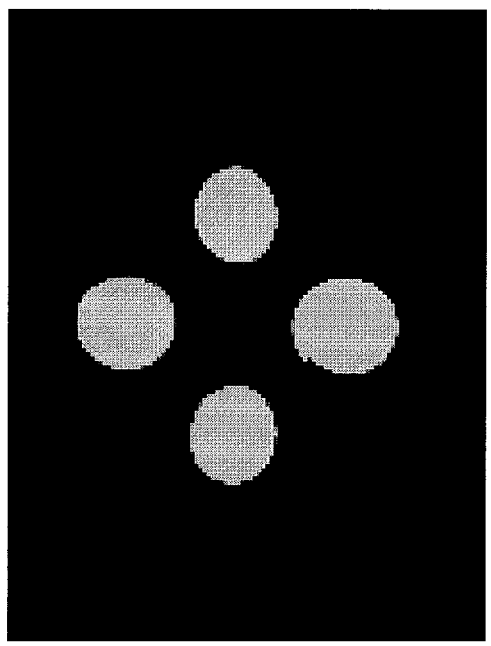
FIG. 13 shows a binary mask, obtained by thresholding the acquired signal of FIG. 12 which identifies components of the signal corresponding to an optical signal (e.g., fluorescence).

The calibration procedure developed for this system, outlined in FIG. 11, reflects both a standard approach to sensor calibration and anticipates new approaches aimed at simplifying calibration including the concept of "calibration over-air".

The calibration procedure allows the user to perform an in-situ characterisation of the sensor system before it is used to carry out measurements. Firstly, the system is used to acquire 200 the optical signal (image) from an optical sensor chip containing a sample for which the analyte concentration is known. The software identifies the signal from the wells/spots 210 and estimates 220 the background signal present in the camera. The optical signal in each well/spot is then measured 225 by integrating the total signal within each well/spot and subtracting the estimated background signal from each well/spot. The image is then stored 230 on phone. The user is then prompted to enter 235 the known analyte value and this, along with the measured optical signals and other process information are stored 240 to an XML-formatted calibration (CAL) file. The user is then prompted 245 to enter another calibration point, if required.

Following calibration, when the user performs a measurement of an unknown analyte, the software running on the mobile phone measures the optical signal for that unknown analyte and calculates the concentration value (e.g., % $O_2$) corresponding to that optical signal level using the data stored in the calibration file. Typically, this process involves automatically fitting a function to the data stored in the calibration file and/or interpolating the unknown analyte value. It is important to stress that this process can be performed by the mobile phone without the need to transfer any data to a remote location for processing.

Furthermore, there are applications for which in-situ calibration may not be possible or desirable. In such a configuration, the software running on the mobile phone correctly interprets and applies correction data stored in the correction file, which may for example be an XML file, without necessarily any knowledge of the origins of the calibration file itself. Therefore, it is possible that in certain arrangements, the calibration file might be generated at some remote location and transferred to the mobile phone via wireless connection. It will be appreciated that in such an arrangement, calibration files may be centrally generated for different phone types and downloaded as required onto the user's phone by the software The measurements for each well/spot may be recorded in a process history file or record (PHF) for subsequent review. This record may be stored individually within a file or aggregated with others. The record may, for example, be in a standard format such as XML. An exemplary XML record is outlined below in table 1, in which an image is initially identified and characterised, after which the wells/spots contained within the image are identified.

TABLE 1

Sample Process History File (PHF)

```
<?xml version="1.0" encoding="ISO-8859-1" ?>
<Record>
    <ID>20090928_13_29_20</ID>
    <Image>
        <Source>c:\Data\Images\HS_20090928_13_29_20.jpg</Source>
        <Binary>c:\Data\Images\HS_20090928_13_29_20_p.jpg
    </Binary>
        <ROI>
            <Shift>
                <X>10</X>
                <Y>-5</Y>
            </Shift>
            <Displacement>11</Displacement>
            <RotationFactor>87</RotationFactor>
        </ROI>
        <Threshold>123</Threshold>
        <Background>12</Background>
    </Image>
    <Data>
    <Spot>
        <ID>1</ID>
        <Signal>1497387</Signal>
        <Area>6297</Area>
        <Mean>225</Mean>
    </Spot>
    <Spot>
        <ID>2</ID>
        <Signal>1455652</Signal>
        <Area>6135</Area>
        <Mean>225</Mean>
    </Spot>
    <Spot>
        <ID>3</ID>
        <Signal>1731838</Signal>
        <Area>7266</Area>
        <Mean>226</Mean>
    </Spot>
    <Spot>
        <ID>4</ID>
        <Signal>1782603</Signal>
        <Area>7257</Area>
        <Mean>233</Mean>
    </Spot>
    </ Data>
</Record>
```

In order to demonstrate the effectiveness of the present sensing system, some tests were conducted. In particular, an optical sensor chip was constructed with 4 sensor spots. The sensor spots were selected for sensing oxygen. Specifically, each sensor spot consisted of a sol-gel (n-propyltriethoxysilane) matrix doped with ruthenium tris(diphenylphenanthroline), a well-known, oxygen-sensitive fluorescent complex. These sensors operate on the principle of fluorescence quenching, which means that increases in oxygen concentration reduce the fluorescence intensity emitted by each sensor. The preparation of such a sensor is described, for example, in C. Higgins, D. Wencel, C. S. Burke, B. D. MacCraith, and C. McDonagh, "Novel hybrid optical sensor materials for in-breath $O_2$ analysis", Analyst, vol. 133, 2008, pp. 241-247.

The optical signal from these sensor spots was detected and analysed using the optical sensor system described which, in this case, employed a NOKIA N96 camera phone. In the experiment, fluorescence excitation was provided by a blue LED (Roithner Lasertechnik, $\lambda$max=450 nm). The results are shown in FIG. 14. Here, it is clear that a non-linear Stern Volmer curve is being produced for each of the four sensor spots, as expected for the well-established, sol-gel-based oxygen sensor technology used. The difference in response from spot to spot can be attributed to the different spot thicknesses produced using the manual stamp-printing deposition technique.

To further demonstrate the effectiveness of the system, a sensor chip was prepared for Myoglobin antibody detection. Specifically anti-myoglobin antibody (7C3, Hytest) was directly immobilised onto silica nanoparticles (2 mg) doped with tris(2'2-bipyridyl)dichlororuthenium (II) hexahydrate, by modifying the amino-modified nanoparticles with glutaraldehyde. Serial dilutions of the antibody-nanoparticle conjugate were prepared in PBS with concentrations ranging from 100-1500 ug/ml. These solutions were pipetted directly onto the surface of a cleaned glass substrate. A template design was employed to ensure that the pipetting was performed at the required on-chip sensor spot locations. Each template consisted of a reference spot (1500 ug/ml) as an internal control and duplicate spots for each concentration.

Figure 15:
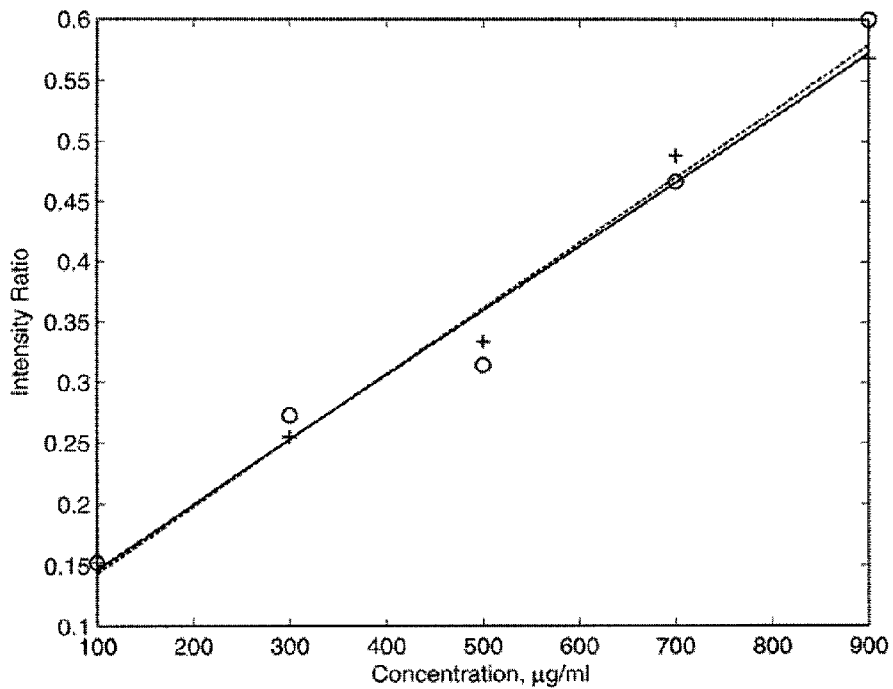
FIG. 15 is the measured response of the mobile phone-based sensor system of FIG. 1 to varying concentrations of anti-myoglobin antibodies labelled with silica nanoparticles. Nanoparticles were doped with the luminescent complex, tris(2'2-bipyridyl)dichlororuthenium (II) hexahydrate.

The output of the sample preparation stage was a number of sensor slides, to each of which a different concentration of nanoparticle-labelled antibodies were bound. Each slide was interrogated in turn using the mobile phone-based sensor platform and the results are shown in FIG. 15. Excitation was provided by coupling light from a blue LED (mounted off-phone) into the end face of the sensor chip, thereby providing evanescent wave excitation of the bound, labelled antibodies.

The two datasets shown are the result of repeat measurements of the fluorescence intensities from five different samples, which were then normalised using the signal detected from the aforementioned control spot. The platform is clearly capable of distinguishing a linear increase in fluorescence intensity that correlates with an increase in antibody concentration from 100-900 ug/ml. Accordingly, it is clear that sensor applications may be implemented using a camera phone as described herein.

A second non-imaging optical configuration is now detailed. In this second configuration, an alternative optical module is employed to provide light to the camera of the mobile phone. The alternative optical module, shown in FIGS. 16 and 17, employs a parabolic outcoupler. The parabolic outcoupler is configured to collect light from the optical sensor chip. This outcoupler allows fluorescence, emitted from a sensor spot on the optical sensor chip, to be coupled out of the optical sensor chip in and redirect it in a substantially collimated annular beam in a direction parallel to the optic axis of the optical sensor module and, in this case, there is no need for the pickup lens arrangement previously described. The outcoupler may be made from an optical material such as, for example, glass or polymer (e.g. Zeonex™/Zeonor™ available from Zeon Chemicals of Louisville, Ky.) and may be fixed to the optical sensor chip or coupled to it using a refractive index matching oil or other similar material In this case, In a similar manner to the previous configuration, a spatial filter may be included within the optical module to reduce stray light. Suitably, this filter will have an annular aperture. A wavelength filter may also be employed in a manner similar to that previously described. To deliver the fluorescence signal to the camera of the phone, focusing lenses may be included as shown. The base of the optical module may be shaped to engage with the docking cradle (previously engaged). Alternatively, the optical module may be shaped to sit directly onto and engage with the surface of the phone or the lens of the camera or both.

A miniature excitation module is provided that may be inserted directly into the outcoupler to provide highly efficient excitation of the sensor spot. The excitation module is shaped to fit inside the inner circumference of the annulus of light coming from the outcoupler. In this respect, the outcoupler may be shaped with a recess and the excitation module may be shaped at the top to co-operate with the shape of the recess. The excitation module is suitably configured to produce a confined excitation spot at the surface of the sensor chip. To achieve this, the excitation module may comprise a LED producing light. One or more lenses may be provided to focus the light from the LED onto the sensor spot. One or more apertures may be provided in layers of opaque material presented in the optical path between the LED and sensor spot which are employed to prevent stray light.

Following excitation, fluorescence emitted from the sensor spot is coupled out of the sensor chip and focused onto the camera of the phone.

Figure 18:
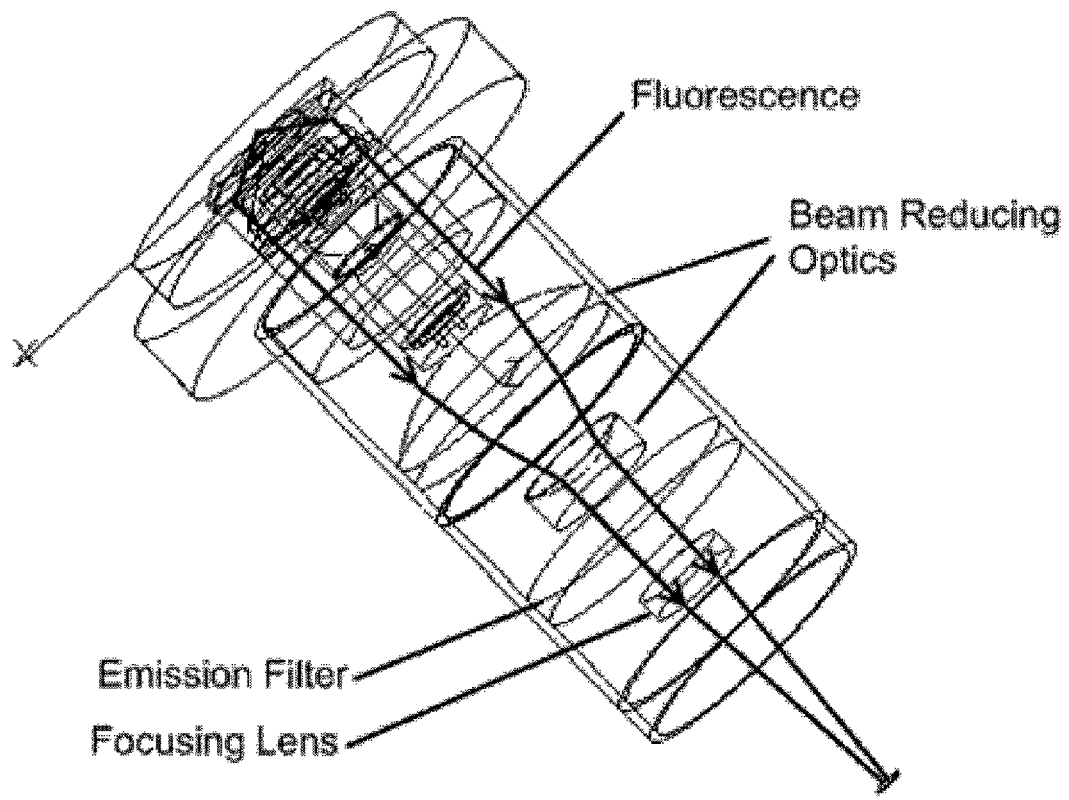
FIG. 18 illustrates a modified form of the arrangement of FIG. 16 and which includes beam reducing optics.

It will be appreciated that the focusing optics used may be changed to alter how the light is focused which may be useful for different applications or to provide compatibility with different handsets. FIG. 18 shows one such variation that includes a beam reducer.

Figure 19:
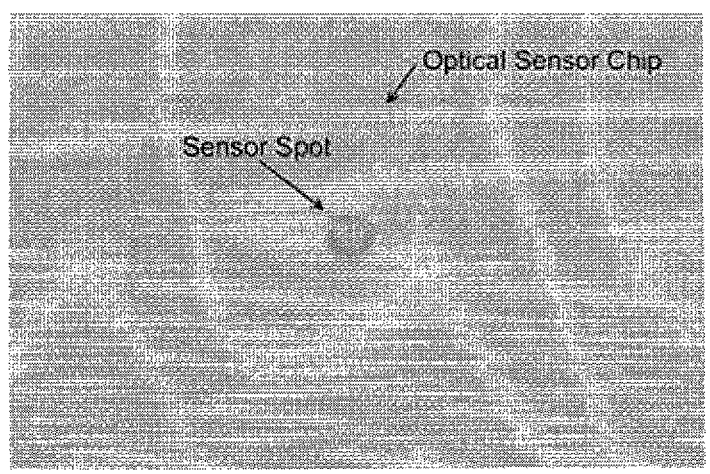
FIG. 19 is a photograph of an exemplary sensor chip having a sensor spot which was employed to demonstrate the efficacy of the present application.

One aspect of the present application is that the non-imaging outcoupler prevents the overall optical system forming an image of the sensor at the camera. An advantage in the use of non-imaging configuration within the context of the present application is that they enhance the amount of optical signal collected. To illustrate this point, a comparison of the total fluorescence signal detected over a range of oxygen concentrations using three optical configurations (one imaging and two non-imaging) was conducted. The first optical configuration was a conventional imaging one, where the camera was placed close to the surface of an optical sensor chip containing a single sensor spot. FIG. 19 shows an example of such an optical sensor chip employing a single fluorescent sensor spot comprising a sol-gel thin film doped with ruthenium tris (diphenylphenanthroline). The optical sensor chip itself is made from the optical polymer Zeonor™. The other two optical configurations employed the two non-imaging optical arrangements described above. To detect the optical signal, the optical sensor chip was placed in a flowcell with a transparent cover and a camera phone (Nokia N96) positioned over the cover of the flowcell so that the sensor spot was in its field of view. An emission filter was placed between the optical sensor chip and the mobile phone camera. The sensor spot was excited using a blue LED (Roithner Lasertechnik, $\lambda_{max}$=450 nm) with an appropriate excitation filter. The oxygen concentration in the flowcell was set to a number of concentrations using mass-flow controllers. An image of the optical sensor chip was acquired using the camera at each of these concentration levels. Each image was then analysed and the fluorescence signal determined.

Figure 16:
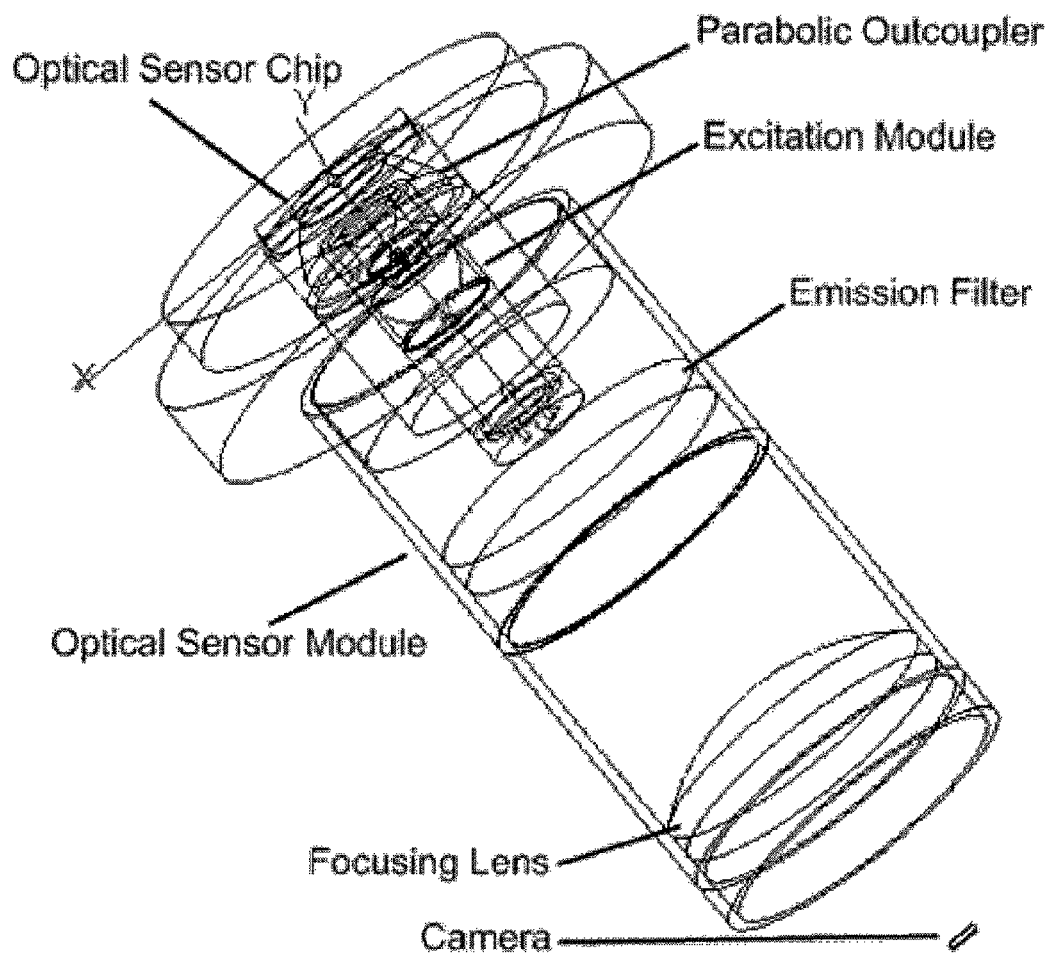
FIG. 16 is an alternative arrangement for an optical module.
Figure 17:
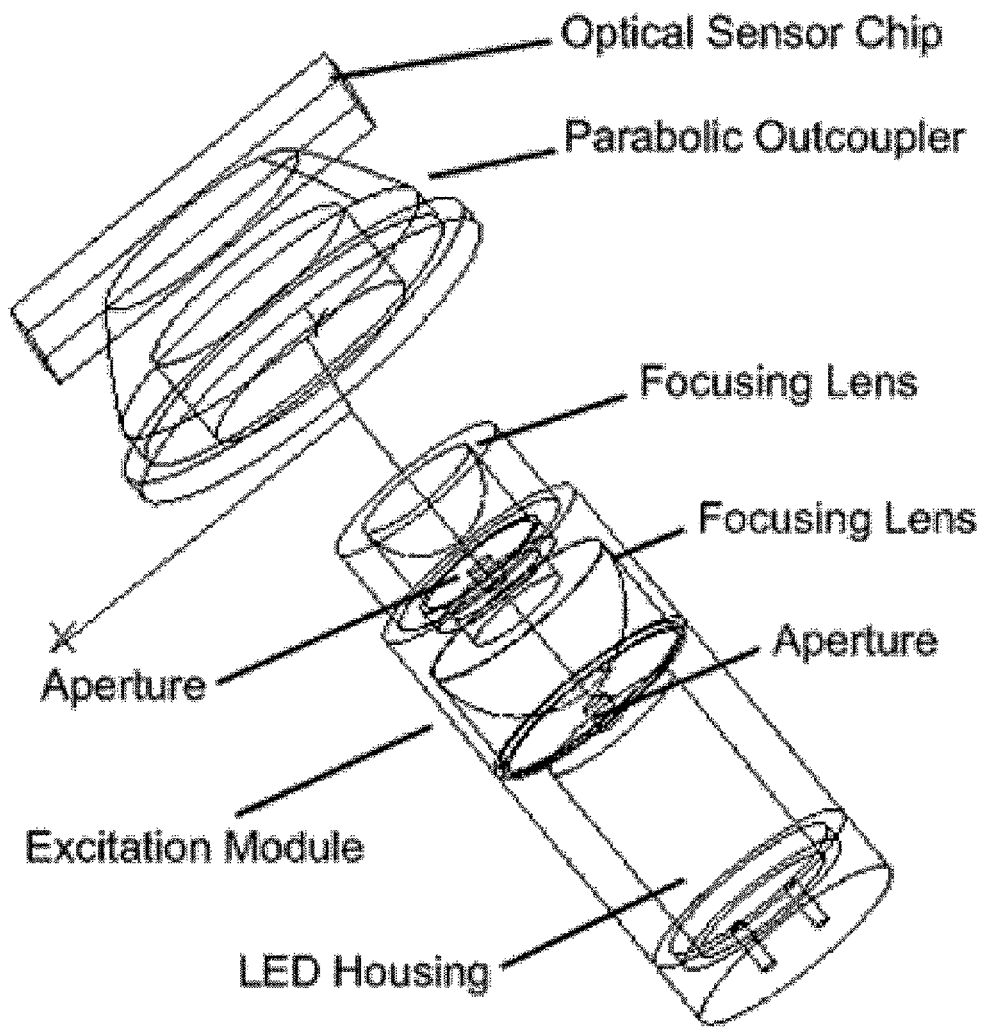
FIG. 17 illustrates aspects of FIG. 16 in greater detail.
Figure 20:
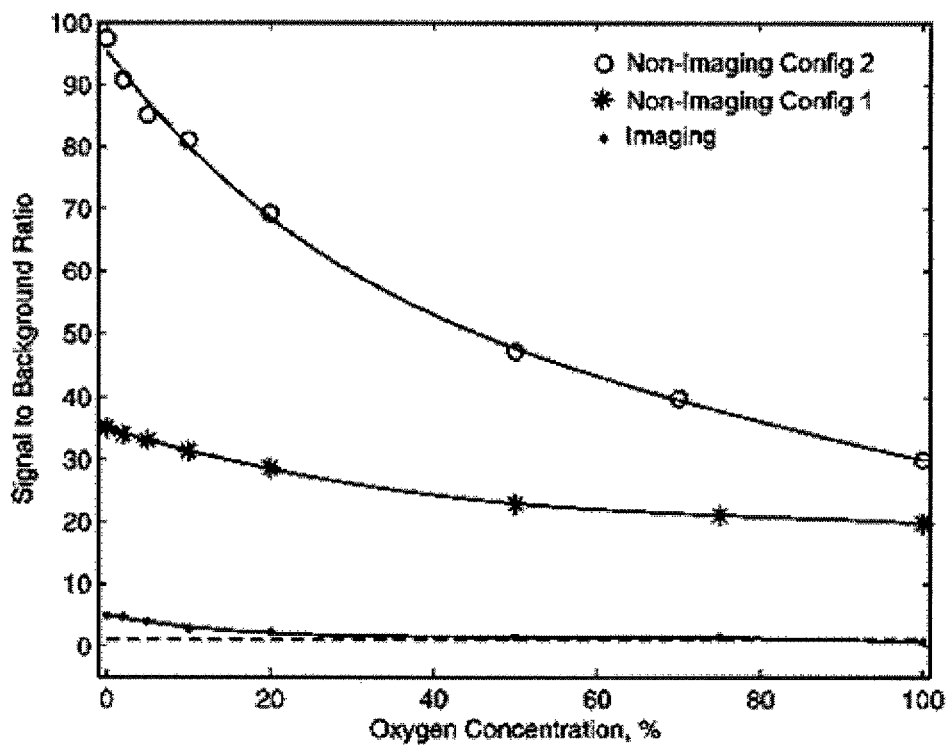
FIG. 20 are results obtained using the sensor chip of FIG. 19 with respect to conventional imaging approach and the proposed non-imaging approach.

The optical sensor chip was then removed from the flowcell and inserted into an optical sensor module containing the non-imaging optics described in FIG. 16 (referred to here as Non-Imaging Config. 2). This optical sensor module was mounted on the mobile phone and a custom flowcell was attached to the top of the sensor module allowing different oxygen concentrations to be delivered to the optical sensor chip. The fluorescence signal was detected by the camera of the mobile phone and analysed for each of the oxygen concentrations. The data acquired using this configuration was then compared to fluorescence measurements obtained using the conventional imaging approach and the non-imaging configuration described in FIG. 8 (referred to here as Non-Imaging Config. 1). FIG. 20 shows a comparison of the signal-to-background ratio for each case. It can be observed that the fluorescence signals detected using both non-imaging optical configurations are substantially greater than the background level (dashed line). These observations are significant in the context of optical sensing and enable the non-imaging configurations to detect lower intensity fluorescence signals than a conventional imaging approach. In the case of the exemplary results corresponding to higher $O_2$ concentrations (lower fluorescence signal levels). For example, using the conventional imaging approach, the ratio of fluorescence signal to average background signal at 20% $O_2$ (ambient oxygen concentration) is 2.3, while for the two non-imaging approaches it is 26 and 70 respectively. Furthermore, by optimization of the sensor spot (i.e. size and indicator concentration) it is possible to further increase the optical signal collected in each of the non-imaging modes.

Figure 21:
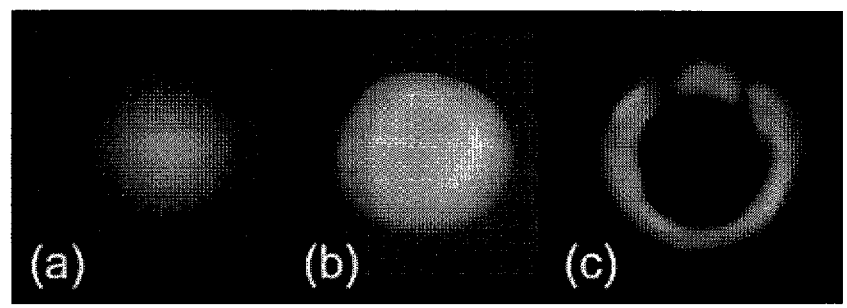
FIG. 21 are photographs illustrating differences between the approaches for which results are shown in FIG. 20 and in particular compares fluorescence signals detected by camera for (a) imaging and (b),(c) non-imaging configurations (in each case the sensor spot size is approximately the same).

As further evidence of the non-imaging nature the optics used in these systems, fluorescence signals acquired by the camera prior to analysis can be compared. FIG. 21(*a*) shows the detected fluorescence signal for the conventional imaging configuration, FIG. 21(*b*) shows the signal for non-imaging configuration 1 and FIG. 21(*c*) shows the signal for non-imaging configuration 2. It can be observed that the imaging signal falls off rapidly in intensity from its centre, however, FIG. 21(*b*) shows how the first non-imaging configuration collects more signal at its edges due to the presence of the outcouplers. In the second non-imaging configuration, the fluorescence signal forms an annular ring of high intensity. In both non-imaging cases, the fluorescence signals do not agree with the signal from the imaging configuration which being an imaging approach is designed to retain spatial information in the image.

This demonstrates that while the camera is itself an image sensor, by counter intuitively viewing it as a collection of individual photodetectors, it may be used in conjunction with non-imaging optics to facilitate sensitive detection of fluorescence.

It will be appreciated that whilst the above description has been described with respect to the placement of the optical module directly in contact with the phone as a single structure that this is not necessarily the case. For example, whilst the optical module may be one of either configurations described above, the optical module may not be in direct contact with the camera and a separate optical path may be provided for providing light from the optical module to the camera of the phone. For example, the light from the optical module may be collected at the entrance to one or more waveguides, such as optic fibres. The exit of the waveguides may be directed to the camera. Similarly, whilst the sensor chip has been described herein in terms of a relatively simple structure, it may equally be a more complex one and may for example be a microfluidic sensor chip in which the delivery of the sample in liquid form to the sensor spots is controlled.

A benefit of the present application is that the outcoupler extracts light from the sensor chip in a non-imaging fashion. As a result, there is significantly more light collected and hence the detection sensitivity of optical testing system when the camera is treated as a collection of individual photo detectors is significantly improved.

Accordingly, the above description is to be taken as being exemplary and the invention is not to be considered limited to the description but is to be understood in the spirit and scope of the claims which follow.

The words comprises/comprising when used in this specification are to specify the presence of stated features, integers, steps or components but does not preclude the presence or addition of one or more other features, integers, steps, components or groups thereof. When used in the present specification the term and/or is to be taken to include all possibilities. Thus for example, A and/or B is to be taken to mean any one of: A on its own, A with B, and B on its own.

The invention claimed is:

1. A non-imaging optical measurement system for measuring luminescence, comprising:
   a personal communications device having an integrated camera;
   an optical module having a plurality of wells or spots to receive a respective one of a plurality of samples for testing, the optical module comprising:
   a plurality of non-imaging outcouplers, each of the non-imaging outcouplers positioned with respect to a respective one of the wells or spots to extract light from a respective one of the samples of the plurality of samples;
   a subsequent optical structure which provides a plurality of distinct optical paths, a separate one of the optical paths for the extracted light from each sample of the plurality of samples, and which directs the extracted light from each sample through the optical module to a respective one of a plurality of unique areas of the camera,
   wherein the personal communications device is configured to extract an intensity measurement from at least one pixel on the camera in respect of each sample and to provide a measurement to a user for each sample from said intensity measurement.

2. The system of claim 1, wherein each outcoupler is comprises at least a respective first lens which is the most-proximal lens to a respective one of the wells or spots, the first lens positioned so that the sample when in a respective well or spot is positioned between a focal point of the first lens and the first lens, at a distance that is less than a focal length of the first lens.

3. The system of claim 1, wherein each outcoupler is comprises a parabolic structure configured to extract the light from the sample as an annular distribution.

4. The system of claim 1, wherein each optical path comprises a lens to collimate the light from each individual sample.

5. The system of claim 4, wherein the lens to collimate the light from each sample is a plano-convex or double-convex lens.

6. The system of claim 4, wherein the subsequent optical structure comprises an emission filter positioned to spectral filter the collimated light.

7. A system according to claim 1, further comprising an integrated light source within the personal communications device and optics arranged to direct light from the integrated light source to illuminate the samples.

8. A system according to claim 7, wherein the integrated light source, is one of:
   a) a light,
   b) a flash, and
   c) a display screen.

9. A system according to claim 8, wherein the system is configured to set the colour or intensity of the integrated light source to a predetermined value when performing a measurement.

10. A system according to claim 1, wherein the optical module further comprises a light source to illuminate the samples.

11. A system according to claim 10, wherein the light source is provided along a central axis of the optical module and between the outcouplers and the camera, the outcouplers spaced laterally from one another.

12. A system according to claim 1, further comprising an optical sensor chip, wherein the plurality of wells or spots are provided on the optical sensor chip, each well or spot providing luminescence in response to the presence of a chemical or biological substance in a sample provided to the well or spot.

13. A system according to claim 1, wherein the system is configured to be used to measure one or more of: oxygen, carbon dioxide, ammonia, carbon monoxide, nitrogen dioxide, lead, ozone, sulphur dioxide, dissolved oxygen, dissolved carbon dioxide, dissolved ammonia, pH, cadmium, mercury, chromium, nitrate, nitrite, metal ions, cations, nitric oxide and Volatile Organic Compounds (VOCs).

14. A system according to claim 1, wherein the system is employed to detect one or more of antibodies, antigens, proteins, DNA, RNA, mRNA, siRNA, miRNA, aptamers, pathogens and cells.

15. A system according to claim 1, further comprising executable software stored in memory on the personal communications device, the executable software providing a correction of pixel intensity using calibration information stored locally in a calibration file.

16. A system according to claim 15, wherein the calibration information is obtained during a calibration procedure performed locally on a testing system.

17. A system according to claim 16, wherein the system is communicatively coupled to at least partially downloaded a calibration file from a remote location.

18. A system according to claim 1, further comprising:
a docking cradle being shaped to receive the personal communications device, the docking cradle being further configured for connection with an optical module.

19. A system according to claim 18, wherein the docking cradle comprises a phone mating section being shaped to receive the body of the personal communications device in a first direction and a docking section mountable on said phone mating section in a second direction transverse to the first direction.

20. A system according to claim 19, wherein each of the phone mating section and the docking section have openings defined therein to allow light from the optical module to pass there through to the camera of the personal communications device.

* * * * *